(12) United States Patent
Fellerman et al.

(10) Patent No.: US 7,358,503 B2
(45) Date of Patent: Apr. 15, 2008

(54) TOMOGRAPHY OF SOLID MATERIALS

(75) Inventors: Andrew Simon Fellerman, Frizington (GB); Brian Andrew Cattle, Wakefield (GB); Robert Michael West, York (GB)

(73) Assignee: British Nuclear Fuels PLC, Cheshire (GB)

( * ) Notice: Subject to any disclaimer, the term of this patent is extended or adjusted under 35 U.S.C. 154(b) by 80 days.

(21) Appl. No.: 10/556,181

(22) PCT Filed: May 13, 2004

(86) PCT No.: PCT/GB2004/002056

§ 371 (c)(1),
(2), (4) Date: Nov. 9, 2005

(87) PCT Pub. No.: WO2004/102172

PCT Pub. Date: Nov. 25, 2004

(65) Prior Publication Data

US 2006/0219932 A1    Oct. 5, 2006

(30) Foreign Application Priority Data

May 14, 2003 (GB) .................................. 0310998.0

(51) Int. Cl.
*G01J 1/42* (2006.01)
(52) U.S. Cl. .................................................. 250/393
(58) Field of Classification Search ................. 250/393
See application file for complete search history.

(56) References Cited

U.S. PATENT DOCUMENTS 4,680,470 A * 7/1987 Heald ........................ 250/358.1
4,983,841 A * 1/1991 Stewart et al. ............ 250/358.1
5,946,220 A * 8/1999 Lemelson .................... 700/273
6,652,661 B2 * 11/2003 Martin .......................... 134/10
6,795,801 B1 * 9/2004 Watkins et al. ................. 703/6

OTHER PUBLICATIONS

Camp et al., "Nondestructive waste-drum assay for transuranic content by gamma-ray active and passive computed tomography", *Nuclear Instruments and Methods in Physics Research A*, v. 495, 2002, pp. 69-83.
Hoyle et al., "Design and application of a multi-modal process tomography system", *Meas. Sci. Technol.*, V. 12, 2001, pp. 1157-1165.
Key et al, "Gas microstrip Detectors for X-ray tomographic flow imaging", *Nuclear Instruments and Methods in Physics Research A*, V. 496, 2003, pp. 504-508.
Olatunbosun, "Multicomponent flow visualization using Compton scattered gamma photons", *Measurement & Control*, vol. 24, Feb. 1991, pp. 11-17.

* cited by examiner

*Primary Examiner*—David Porta
*Assistant Examiner*—Mindy Vu
(74) *Attorney, Agent, or Firm*—Myers Bigel Sibley & Sajovec

(57) ABSTRACT

The invention provides a method for the identification of deposits of solid materials in process plants, the method comprising the creation of a theee-dimensional image by means of tomography, preferably passive tomography, most preferably gamma-ray tomography. Typically, the solid materials comprise gamma-ray emitting solid materials and the process plants comprise nuclear process plants. In general, the deposits of solid materials are deposited from liquid media, and the liquid media preferably comprise aqueous suspensions of these materials. The method is particularly applicable to highly active nuclear waste liquids in High Activity Storage Tank (HAST) applications, and offers significant advantages over the methods of the prior art, since it comprises a non-invasive technique which does not require the prior installation of a detector in the vessel from which data are to be obtained.

22 Claims, No Drawings

TOMOGRAPHY OF SOLID MATERIALS

RELATED APPLICATION

This application is a national phase application of PCT International Application PCT/GB2004/002056, filed May 13, 2004, and published in English on Nov. 25, 2004 as International Publication No. WO 2004/102172, which claims priority from British Application No. 0310998.0, filed May 14, 2003. These disclosures are hereby incorporated by reference herein in their entireties.

This invention is concerned with a novel, non-invasive means for the detection and three-dimensional imaging of quantities of solids materials deposited from liquid media in industrial equipment, particularly storage vessels. More specifically, it relates to a novel application of high energy gamma-ray tomography to the identification of the location and geometry of accumulations of gamma-emitting solids from nuclear process plants. Such accumulations are encountered in organic and aqueous suspensions, and in gaseous streams, most particularly in waste treatment processes in the nuclear processing industry.

The storage and transfer of gamma-emitting radionuclides is common in the nuclear processing industry. Consequently, the identification of the location and approximate geometry of accumulations of gamma-emitting solids is of interest, to ensure operability of plant and safe storage of highly emitting materials. This is particularly true in the case of so called "High Activity Storage Tank" (HAST) applications, wherein significant volumes of highly active liquors from nuclear fuel reprocessing, which have been concentrated up to 100-fold by evaporation, are stored in cooled double-walled tanks, generally constructed from stainless steel.

The known technology in this field has generally relied on the proven effectiveness of the installed agitation equipment, and on temperature detection as the monitoring means. Thus, it has been necessary to install temperature detectors in the equipment, the detectors having to be located in the same positions as the solid deposits, and their effective operation relying on the presence of sufficient deposited material to promote a temperature rise of the material above that of the bulk liquor which is sufficiently significant to be detectable.

Naturally, there are disadvantages with this approach. In the first instance, it is necessary for the relevant temperature detection means to be installed in the equipment during construction. Furthermore, it is necessary that the equipment designer should be able to accurately predict the correct location for the detector within the equipment; clearly, the detector must be located at a position, or positions, where solids deposits will occur if it is to be able to perform its function effectively, but it may not always be possible to make such predictions with complete accuracy at the outset. Consequently, it is quite likely that, in use, this means of detection may completely fail to identify some deposits, if these occur in locations which are not provided with a detector. In addition, of course, it has to be borne in mind that since the method relies on temperature increases as the means of detection, there is the possibility that temperatures may reach undesirably high levels before operators are alerted to the presence of accumulated solids deposits.

Clearly, therefore, there is a requirement for a more efficient, safer and preferably non-invasive means to allow for the ready detection of solids deposits in such circumstances, and it is this objective which the present invention seeks to address. The invention thus overcomes the deficiencies of the prior art, and facilitates the convenient identification of the location and geometry of accumulations of gamma-emitting solids, thereby significantly enhancing the prospects for the safe storage of highly gamma-emitting materials.

The present invention relies on a novel and inventive application of the technique of tomography, more specifically gamma-ray tomography. Tomography first found significant practical application in the medical field, where X-ray tomography allowed for non-intrusive diagnoses to be performed by creating cross-sectional images from scanned data obtained from the human body. The technique of tomography relies on compiling a series of data measurements from an array of sensors and then processing the data using an appropriate image reconstruction algorithm run on suitable computer hardware in order to generate a suitable image on a screen.

Following the initial research in the field of medical imaging, a number of applications of tomographic imaging of process equipment were described, but generally these involved using ionising radiation from X-ray or isotope sources, and were not found to be satisfactory for the majority of process applications on a routine basis because of the high cost involved and safety constraints. Most of the radiation-based methods used long exposure times which meant that dynamic measurements of the real time behaviour of process systems were not feasible. Such methods furnished examples of active tomographic techniques, wherein an external signal is provided and the response of a medium to the signal is measured.

However, as well as developing and refining these active tomographic methods, later work also focused on an alternative tomographic approach, wherein the variation of some inherent property of a medium was assessed. Several methods of this type—known as passive process tomography systems—were developed, and may rely on, for example, the measurement of electrical parameters, such as capacitance, impedance and resistance, by means of an array of sensors placed around the periphery of a process vessel, to create an image of the concentration and movement of components inside, both cost-effectively and in real-time. Measurements were reconstructed to form 2- or 3-dimensional images, providing information to monitor processes and improve yields, quality, efficiency and overall control. Electrical impedance tomography also found application as a safe, low-cost method for imaging the human body.

Process tomography has now been applied to many types of processes and unit operations. Depending on the sensing mechanism used, it is non-invasive, inert and non-ionising, and is therefore applicable in the processing of raw materials, in large-scale and intermediate chemical production, and in the food and biotechnology areas. A number of tomographic processes have become available for studying complex multiphase phenomena. These include, for example, infrared and optical tomographic systems, positron emission tomography (PET), magnetic resonance imaging (MRI), and sonic or ultrasonic tomographic systems, and various of these tomograpic systems have been used to image multiphase processes such as fluidisation, pneumatic conveying, liquid/liquid and gas/liquid mixing and solid/liquid separation occurring in pipelines, stirred reactors, fluidised beds, mixers and separators.

The use of the technique of gamma-ray tomography for the study of liquid holdup distribution in large packed columns has been disclosed by F Yin, A Afacan, K Nandakumar and K T Chuang, *Chem. Eng Process.*, 41 (2002), 473-483. The method involved the measurement of two liquid flow rates by means of horizontal scans, taken at two vertical positions. Yin et al also report the successful application of this technique in the troubleshooting of distillation columns, the measurement of gas holdup profiles in bubble columns and the measurement of local porosity distribution in packed columns.

A more interesting application of gamma-ray tomography is in the assay of drums containing radioactive waste. The Waste Inspection Tomography for Non-Destructive Assay (WIT-NDA) system developed by Lawrence Livermore National Laboratory and Bio-Imaging Research combines active and passive computed tomography and nuclear spectroscopy to accurately quantify all detectable gamma-rays emitted from waste containers. This technique, disclosed in *Nuclear Engineering International,* 46(59), 18, has been used for the non-destructive examination and assay of radioactive waste since 1999.

However, whilst the WIT-NDA system has been found to be extremely useful for the examination of nuclear waste materials stored in drums, the system only has limited applicability, since such waste is inevitably in solid form, for example encapsulated in concrete or vitrified with glass-forming materials. Clearly, in such circumstances, the waste materials are immobilised within a solid matrix and the situation is very different to that addressed by the present inventors, who have sought to identify solid deposits and accumulations which occur in fluid media, specifically liquid suspensions of the said materials, wherein there is a degree of mobility of all the components.

Particular difficulties may be encountered in situations where bulk fluid media, particularly bulk liquid media, are being handled in large-scale storage tanks, since access for measurements may be severely limited due to a high-radiation environment existing in the vicinity of the tanks. In such circumstances, it is important to know whether or not the contents of the tank are well mixed, which is the desirable situation, or if some of the solid has come out of suspension and deposited at some location within the tank.

Surprisingly, the present inventors have now found that it is possible to successfully apply the technique of tomography to the identification of accumulations of solid materials in nuclear process plants. Since the present application comprises a passive tomographic technique, wherein the shape, signal strength and distribution of the source material is unknown, the problems of implementation of such a technique are that much greater, but the inventors have found that it is possible to achieve accurate images of accumulations of material in such circumstances by means of this technique.

Additionally, a method has been found which facilitates the production of two images, one of which shows the distribution of the sources of the emissions, whilst the other shows the structure of the attenuating medium between the sources and the detectors.

Various aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items.

Unless otherwise defined, all technical and scientific terms used herein have the same meaning as commonly understood by one of ordinary skill in the art to which this invention belongs. All publications, U.S. patent applications, U.S. patents and other references cited herein are incorporated by reference in their entireties with respect to the text referenced by the citation.

Thus, according to the present invention, there is provided a method for the identification of deposits of solid materials in process plants, said method comprising the creation of a three-dimensional image by means of tomography. Specifically, the method provided by the present invention comprises passive tomography, wherein there is no requirement for the application of an external field, and the technique relies on the emission of radiation by the system under investigation. The emitted radiation may be radioactive in nature; in the preferred situation, said radiation comprises gamma-radiation, and the preferred monitoring technique comprises gamma-ray tomography.

More specifically, said solid materials comprise gamma-ray emitting solid materials and said process plants comprise nuclear process plants. Said deposits of solid materials comprise deposits which are deposited from gaseous media or, more particularly, from liquid media. Typically, said liquid media comprise liquid suspensions of said materials, for example, suspensions of said materials in organic solvents but, more preferably, aqueous suspensions of said materials. Most preferably said liquid suspensions of said materials comprise highly active nuclear waste liquids.

Said deposits typically comprise accumulations of said solid materials which occur in, for example, storage tanks, particularly large scale storage tanks. Alternatively, it is envisaged that said deposits could occur in pipework used to transfer the liquid media between vessels. The method of the present invention, however, finds particular applicability in the monitoring of radioactive waste in "High Activity Storage Tank" (HAST) applications.

The identification of said solid deposits typically involves the identification of the location of said deposits and the identification of the geometry of said deposits. Said identifications are facilitated by the creation of three-dimensional images of the deposits by means of gamma-ray tomography. Thus, by means of image reconstruction, gamma-emission tomography becomes a powerful tool for industries handling radioactive materials. Optimum results are achieved with materials stored in storage tanks having a diameter of around two metres or less, in which case 100% imaging may be achieved.

The method of the present invention relies on the measurement, by means of an array of sensors, of emissions, preferably gamma-ray emissions, from process equipment, which typically comprises a storage tank, and the subsequent manipulation of the obtained data by means of a suitable computer algorithm in order to generate a three-dimensional image. The method involves the computation of a solution to the Boltzmann equation for gamma-ray transport. This exercise is in the class of inverse problems, whereby the distribution of the source terms is derived on the basis of measurements made at the boundary of the process plant.

As previously discussed, the method of the present invention finds particular application in the identification of solid accumulations in storage tanks, but is also valuable in detecting blockages which may occur in pipework, and for the detection of leaks which might be occurring from pipework, storage tanks, or any other vessels.

It also finds application in monitoring the efficiency of stirring or other forms of agitation which are being used in vessels, since any unwanted deposition of material can be readily identified.

In addition, as observed earlier, the method can be adapted for the production of two images, the first of these showing the distribution of the sources of the gamma-ray emissions, whilst the other depicts the structure of the attenuating medium between the sources and the detectors.

The technique offers significant advantages over the methods of the prior art which were used for the monitoring of such solid deposits, most particularly in view of the fact that it comprises a non-invasive technique which does not require the prior installation of a detector in the vessel from which data are to be obtained. In addition, it allows for the investigation of a system with no prior knowledge of its contents, unlike the Waste Inspection Tomography for Non-Destructive Assay (WIT-NDA) system of Lawrence Livermore National Laboratory and Bio-Imaging Research, which has previously been discussed.

The method of the present invention is also distinguished over various methods of the prior art in that it relies only on the emission, rather than the transmission, of radiation; furthermore, unlike the known techniques which provide two-dimensional, images, the present technique facilitates the production of images in three dimensions.

The invention claimed is:

1. A method for the identification of deposits of solid materials in process plants, said method comprising the creation of a three-dimensional image by means of tomography.

2. A method as claimed in claim 1 wherein said tomography comprises passive tomography.

3. A method as claimed in claim 1 wherein said tomography comprises gamma-ray tomography.

4. A method as claimed in claim 3 wherein said solid materials comprise gamma-ray emitting solid materials and said process plants comprise nuclear process plants.

5. A method as claimed in claim 1 wherein said deposits of solid materials comprise deposits which are deposited from gaseous media.

6. A method as claimed in claim 1 wherein said deposits of solid materials comprise deposits which are deposited from liquid media.

7. A method as claimed in claim 6 wherein said liquid media comprise liquid suspensions of said solid materials.

8. A method as claimed in claim 7 wherein said liquid suspensions of said solid materials comprise suspensions of said solid materials in organic solvents.

9. A method as claimed in claim 7 wherein said liquid suspensions of said solid materials comprise aqueous suspensions of said solid materials.

10. A method as claimed in claim 9 wherein said aqueous suspensions of said solid materials comprise highly active nuclear waste liquids.

11. A method as claimed in claim 1 wherein said deposits comprise accumulations of said solid materials occurring in storage tanks.

12. A method as claimed in claim 11 wherein said storage tanks comprise large scale storage tanks.

13. A method as claimed in claim 11 wherein said storage tanks have a diameter of around two meters or less.

14. A method as claimed in claim (1) wherein said deposits comprise accumulations of said solid materials in pipework used to transfer liquid media between vessels.

15. A method as claimed in claim 1 wherein the identification of said solid deposits comprises the identification of the location of said deposits and the identification of the geometry of said deposits.

16. A method as claimed in claim 1 which comprises the measurement of emissions from process equipment and the manipulation of the obtained data in order to generate a three-dimensional image.

17. A method as claimed in claim 16 wherein said measurement of emissions is achieved by means of an array of sensors.

18. A method as claimed in claim 16 wherein said measurement of emissions comprises measurement of gamma-ray emissions.

19. A method as claimed in claim 16 wherein said manipulation of the obtained data in order to generate a three-dimensional image comprises manipulation by means of a computer algorithm.

20. A method as claimed in claim 16 wherein said manipulation of the obtained data involves the computation of a solution to the Boltzmann equation for gamma-ray transport.

21. A method for the identification of deposits of solid materials in process plants, said method comprising the creation of a three-dimensional image by means of tomography wherein said deposits comprise accumulations of said solid materials occurring in storage tanks and said storage tanks are large scale storage tanks comprising High Activity Storage Tanks.

22. A method for the identification of deposits of solid materials in process plants, said method comprising the creation of a three-dimensional image by means of tomography, wherein said tomography comprises gamma-ray tomography which is adapted for the production of two images, the first of these showing the distribution of the sources of gamma-ray emissions and the other depicting the structure of the attenuating medium between the sources and the detectors.

* * * * *